United States Patent
Colone

(10) Patent No.: US 6,620,190 B1
(45) Date of Patent: *Sep. 16, 2003

(54) RADIALLY EXPANDABLE POLYTETRAFLUOROETHYLENE

(75) Inventor: William M. Colone, Phoenix, AZ (US)

(73) Assignee: Impra, Inc., a subsidiary of C.R. Bard, Inc., Tempe, AZ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/773,281

(22) Filed: Dec. 26, 1996

Related U.S. Application Data

(63) Continuation of application No. 08/588,228, filed on Jan. 18, 1996, now abandoned, which is a continuation of application No. 08/239,239, filed on May 6, 1994, now abandoned.

(51) Int. Cl.⁷ .......................... A61F 2/06; A61M 29/00; B32B 27/32; C08F 14/18
(52) U.S. Cl. .................. 623/1.1; 623/1.11; 623/1.12; 623/1.14; 623/1.15; 623/1.21; 623/1.25; 606/194; 606/195; 526/255; 428/422; 428/304.4; 428/398
(58) Field of Search .................. 526/255; 428/422, 428/398, 304.4; 623/1.1, 1.11, 1.12, 1.2, 1.14, 1.15, 1.21, 1.25; 606/194, 195

(56) References Cited

U.S. PATENT DOCUMENTS

| | | | |
|---|---|---|---|
| 3,008,187 A | 11/1961 | Slade | 606/191 |
| 3,260,774 A | 7/1966 | Harlow | 606/198 |
| 3,389,201 A | 6/1968 | Alsup et al. | 128/343 |
| 3,391,221 A | 7/1968 | Gore et al. | 128/343 |

(List continued on next page.)

FOREIGN PATENT DOCUMENTS

| | | |
|---|---|---|
| DE | 3918736 A1 | 12/1990 |
| EP | 0 221 570 B1 | 5/1987 |
| EP | 0 232 543 A2 | 8/1987 |
| EP | 0 267 719 A2 | 5/1988 |
| EP | 0 269 449 A2 | 6/1988 |
| EP | 0 335 341 A1 | 10/1989 |
| EP | 0 461 791 A1 | 12/1991 |
| EP | 0 551 179 A1 | 7/1993 |
| GB | 1 506 432 | 4/1978 |
| JP | 61-17648 | 4/1955 |
| JP | 58-44378 | 2/1979 |
| JP | 6-1143 | 4/1980 |
| JP | 62-152467 | 7/1987 |
| JP | 2-69220 | 3/1990 |
| WO | WO 91/07203 | 5/1991 |
| WO | WO 91/13648 | 9/1991 |
| WO | WO 93/17636 | 9/1993 |
| WO | WO 94/01056 | 1/1994 |
| WO | WO 94/12136 | 6/1994 |
| WO | WO 94/13224 | 6/1994 |

OTHER PUBLICATIONS

Julio C. Palmaz, "Uses of balloon expandable stents in combination with PTFE", W.B. Saunders Company, Ltd., pp. 36–42, 1994.

U.S. Ser. No. 08/135,226, Andersen et al., "Medical Stents for Body Lumens Exhibiting Peristaltic Motion" Oct. 13, 1993.

U.S. Ser. No. 07/960,584, Andersen et al., "Medical Stents for Body Lumens Exhibiting Peristaltic Motion" Oct. 13, 1992.

*Primary Examiner*—Christopher S. F. Low
*Assistant Examiner*—Abdel A. Mohamed
(74) *Attorney, Agent, or Firm*—Morrison & Foerster

(57) ABSTRACT

Extruded, stretched, sintered tubular PTFE materials are produced which are suited for use in the medical field as liners and covers for expandable stents. The PTFE materials have an unusually low REC (Radial Expansion Coefficient) and RER (Radial Expansion Ratio).

15 Claims, 1 Drawing Sheet

U.S. PATENT DOCUMENTS

| | | | |
|---|---|---|---|
| 3,953,566 A | 4/1976 | Gore | 174/102 R |
| 3,962,153 A | 6/1976 | Gore | 174/102 R |
| 4,025,679 A | 5/1977 | Denny | 621/1 |
| 4,104,394 A | 8/1978 | Okita | 621/127 |
| 4,110,392 A | 8/1978 | Yamazaki | 264/127 |
| 4,187,390 A | 2/1980 | Gore | 174/102 R |
| 4,229,838 A | 10/1980 | Mano | 999/1.4 |
| 4,250,138 A | 2/1981 | Okita | 264/568 |
| 4,277,429 A | 7/1981 | Okita | 264/127 |
| 4,283,448 A | 8/1981 | Bowman | 428/36 |
| 4,332,035 A | 6/1982 | Mano | 999/1.4 |
| 4,385,093 A | 5/1983 | Hubis | 428/316 |
| 4,478,665 A | 10/1984 | Hubis | 156/229 |
| 4,482,516 A | 11/1984 | Bowman et al. | 264/127 |
| 4,496,507 A | 1/1985 | Okita et al. | 264/127 |
| 4,560,374 A | 12/1985 | Hammerslag | 604/49 |
| 4,576,869 A | 3/1986 | Malhotra | 428/502 |
| 4,598,011 A | 7/1986 | Bowman | 428/221 |
| 4,733,665 A | 3/1988 | Palmaz | 128/343 |
| 4,743,251 A | 5/1988 | Barra | 623/1 |
| 4,776,337 A | 10/1988 | Palmaz | 128/343 |
| 4,826,725 A | 5/1989 | Harlow | 428/375 |
| 4,830,062 A | 5/1989 | Yamamoto et al. | 138/177 |
| 4,876,051 A | 10/1989 | Campbell et al. | 264/127 |
| 4,877,661 A * | 10/1989 | House et al. | 428/34.9 |
| 4,922,905 A | 5/1990 | Strecker | 128/343 |
| 4,973,609 A * | 11/1990 | Browne | 521/81 |
| 5,024,671 A | 6/1991 | Tu et al. | 623/1 |
| 5,026,513 A | 6/1991 | House et al. | 264/127 |
| 5,061,276 A | 10/1991 | Tu et al. | 623/1 |
| 5,071,609 A * | 12/1991 | Tu et al. | 526/255 |
| 5,078,726 A | 1/1992 | Kreamer | 606/194 |
| 5,098,625 A | 3/1992 | Huang et al. | 264/127 |
| 5,108,424 A | 4/1992 | Hoffman, Jr. et al. | 623/1 |
| 5,110,527 A | 5/1992 | Harada et al. | 264/127 |
| 5,122,154 A | 6/1992 | Rhodes | 606/198 |
| 5,123,917 A | 6/1992 | Lee | 623/1 |
| 5,217,483 A | 6/1993 | Tower | 606/198 |
| 5,219,355 A | 6/1993 | Parodi et al. | 606/191 |
| 5,238,618 A | 8/1993 | Kinzer | 264/41 |
| 5,258,020 A | 11/1993 | Froix | 623/1 |
| 5,308,664 A | 5/1994 | House et al. | 428/34.9 |
| 5,316,023 A | 5/1994 | Palmaz et al. | 128/898 |
| 5,360,443 A | 11/1994 | Barone et al. | 623/1 |
| 5,383,928 A | 1/1995 | Scott et al. | 623/1 |
| 5,389,106 A | 2/1995 | Tower | 606/198 |
| 5,425,765 A | 6/1995 | Tiefenbrun et al. | 623/1 |

* cited by examiner

RADIALLY EXPANDABLE POLYTETRAFLUOROETHYLENE

This is a continuation of application Ser. No. 08/588,228 filed Jan. 18, 1996, now abandoned; which is a continuation application of Ser. No. 08/239,239, filed on May 6, 1994 (abandoned).

FIELD OF THE INVENTION

This invention relates to polytetrafluoroethylene (hereinafter PTFE) materials which, after being radially expanded, retain their the structural integrity.

More particularly, the invention relates to extruded, stretched, sintered tubular PTFE materials suited for use in the medical field as liners and covers for. expandable stents.

BACKGROUND OF THE INVENTION

The use of expandable endovascular stents to open and support aortic blood vessels is well known in the art. Such stents, which are typically made from stainless steel, are thrombogenic and tend to occlude due to growth of tissue through the stent into the blood vessel. The length of such stents is also limited because of their rigidity. Consequently, liners and covers have been sought for use in conjunction with metallic stents in order to shield the stent and to extend the length of anatomy which can be treated with the stent. The development of acceptable stent liners or covers has been slow because the liners or covers preferably must (1) expand with the stent, (2) be non-thrombogenic, (3) be biocompatible, (4) be inert, (5) have a low profile with the ability to expand up to about four times its original dimension, (6) be expandable at low pressures of less than five to ten atmospheres to reduce the risk of injury to the patient, (7) retain its physical properties and structural strength after being expanded, (8) generally not alter its length after being expanded, (9) be impervious to blood at physiological pressures, (10) conform to host anatomy when expanded, (11) resist the growth of bodily tissue therethrough, (12) be able to carry radiopaque markings for location during fluoroscopy.

Paste-formed, extruded tubular PTFE products are well known, as are paste extrusion and paste forming manufacturing processes for producing such products. During such manufacturing processes, a PTFE resin is mixed with a liquid lubricant. A preformed resin—lubricant charge is then produced and extruded through an annular orifice to produce an unsintered PTFE tube. The extruded tube is heated to remove the lubricant and produce a porous, unsintered PTFE tube. The tube typically has a density of from 1.5 to about 1.75 gm/cc and accompanying porosities of 39% to 26%. If the unsintered tube is sintered by heating the tube to a temperature above its crystalline melting temperature, a nonporous tube results. See U.S. Pat. Nos. 3,953,566, 3,962,153, 4,110,392, 4,187,309, 4,283,448, 4,385,093, 4,478,665, 4,482,516, 4,877,661, and 5,026,513.

In the medical field, PTFE products are used as replacement veins and arteries. PTFE is inert, is non-thrombogenic, and has other characteristics desirable for a stent cover or liner. Commercially available PTFE medical tubular products have, however, significant radial strength and are not readily dilated. Conventional PTFE tubes typically have a high radial strength and rapidly lose their tensile strength and become weak and thin after being dilated by only small amounts.

Accordingly, it would be highly desirable to provide improved PTFE products which can be readily expanded and which, after being expanded, substantially retain their tensile strength and other physical properties which make the use of PTFE in the body desirable.

Therefore, it is a principal object of the invention to provide improved PTFE products which are amenable to use as liners and covers for expandable stents.

A further object of the invention is to provide improved tubular PTFE products which substantially retain their structural integrity after the products are radially expanded.

Another object of the invention is to extend the length of anatomy which can be treated with an expandable

SUMMARY OF THE INVENTION

I have discovered new PTFE products and a process and composition for producing the same. The new PTFE products can be significantly expanded to configurations which retain their structural integrity and which substantially retain their tensile strength and other desirable physical properties. As discussed in detail in the examples below, the new PTFE products have an unusually low REC (Radial Expansion Coefficient) and RER (Radial Expansion Ratio) which function to permit thin-walled PTFE tubes to expand about 50% to 400% before, the tubes lose their structural integrity and suffer a rapid decline in tensile strength.

The following examples are presented to illustrate the presently preferred embodiments of and practice of the invention and not by way of limitation of the scope of the invention.

DETAILED DESCRIPTION OF THE INVENTION

Examples 1–17, below, concern expandable PTFE material formed as a result of stretching and subsequent sintering.

EXAMPLE 1

One hundred grams of FLUON CD123 resin produced by ICI Americas, Inc. was sifted through a No. 10 sieve and then blended at room temperature with twenty-five grams of ISOPAR M solvent produced by Exxon Corporation to produce a preform blend. Other lubricants well known in the art includes VM&P NAPHTHA (boiling point (bp) 118–130° C.), ISOPAR (Registered trademark of Exxon Corporation), ISOPAR 3 G (bp 159–174° C.), ISOPAR H (bp 176–189° C.), Low Odor Paraffin Solvent (bp 191–246° C.), and SHELLSOL (Trademark of Shell Oil) K.

The resulting preform blend was allowed to sit for over eight hours before being re-sifted through a No. 10 sieve. The lubricant level (LL) equals the weight of solvent used divided by the weight of resin used, which means the lubricant level utilized in this Example 1 was 25%. In the practice of the invention the lubricant level is normally in the range of 16% to 35%, and is presently preferably in the range of about 18% to 25%.

BRIEF DESCRIPTION OF THE DRAWINGS

Referring now to FIG. 1, a preform charge 10 was created by compacting the preform blend under 200 to 400 psi for approximately one minute in a stainless steel cylinder containing a center shaft. The center shaft extended along the centerline X of the cylinder and was concentric with the cylinder. The resulting preform charge 10 was a hollow cylindrical mass having a doughnut shaped circular cross sectional area 13, as shown in FIG. 1. The cylindrical hollow mid-section 15 in the preform charge 10 was occupied by the center shaft. The preform charge 10 was then loaded into a cylindrical barrel in a ram extruder and was extruded into several individual lengths of cylindrical thin-walled tubing 11 at a reduction ratio (RR) of 125:1. The total length of tubing 11 produced from the preform charge 10 was about twenty feet. The extruded tubing 11 had a microstructure characterized by nodes interconnected by fibrils. The reduction ratio equals the ratio of the cross sesectional area 13 of the preform charge 10 to the cross sectional area 14 of the wall of the tubing 11. In the practice of the invention, the RR is less than 200 or 300 to 1; preferably equal to or less than 125:1. The ratio of the RR to the LL in the practice of the invention is preferably less than five. In prior art preform blends the ratio of the RR to the LL is normally greater than five, and is typically nine or greater.

Figure 1:
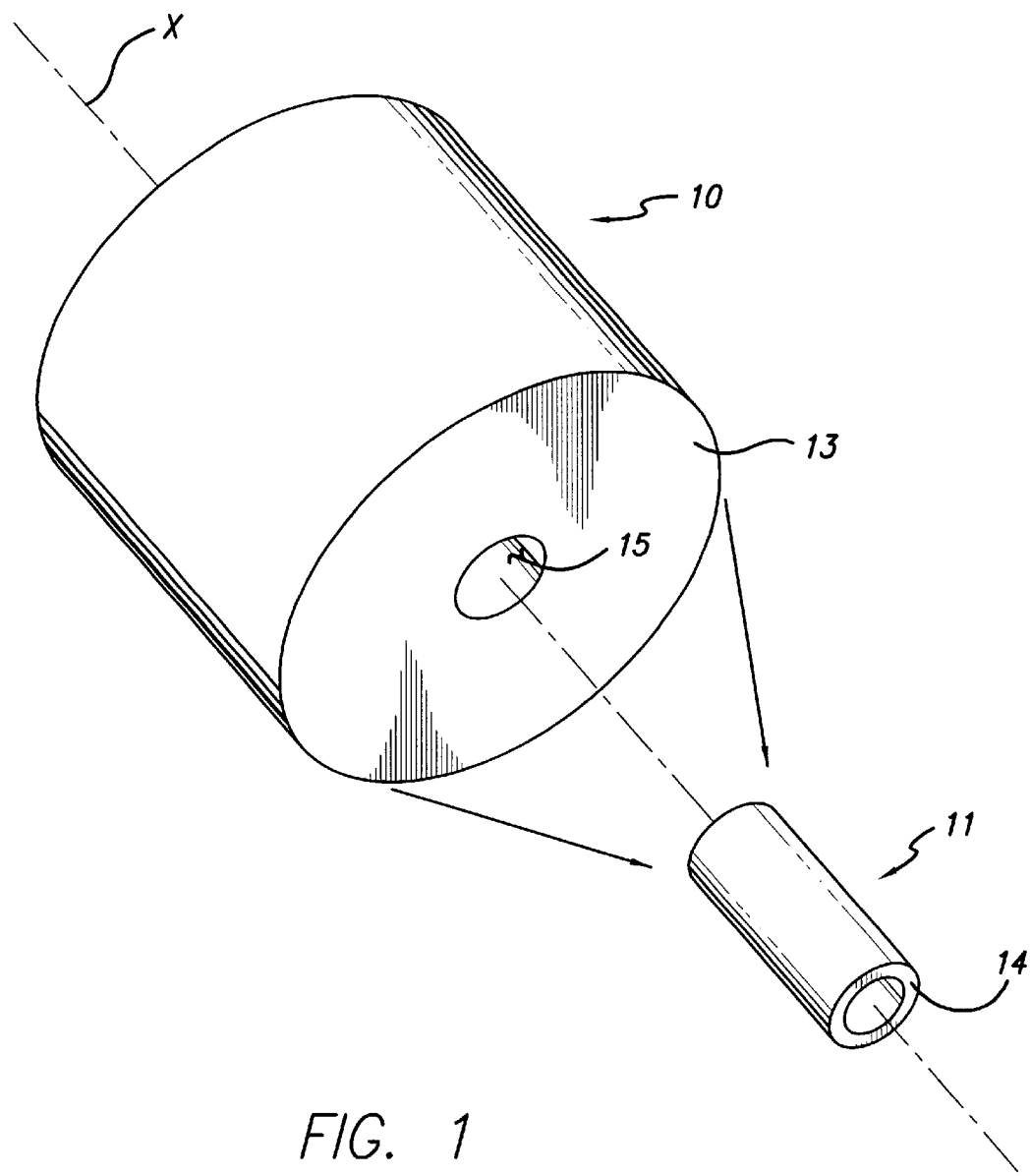
FIG. 1 is a radially expandable stent.

The solvent was removed from the extruded tubing by placing the tubes in a forced air circulation electric oven at 255 degrees C. for thirty minutes As used herein, the length of the tube after it is extruded and heated at 255 degrees C. to remove the solvent is termed the original length of the tube.

After being heated to 255 degrees C., each tube was heated to 290 degrees C. for five minutes and then stretched longitudinally at rate of about 100% per second to a length four times the original length of the tube. Each tube can, if desired, be stretched at a rate in the range of 5% to 500% per second and stretched to a length in the range of two to six times the original length of the tube.

The stretched porous tubes were then sintered at approximately 300 degrees C. for forty-five to 90 seconds. The sintering crystallized the PTFE and increased the strength of the porous tubes. During sintering each end of the tubes was restrained to prevent longitudinal shrinkage of the tube. The resulting stretched, sintered, porous tubes consisted essentially of highly crystalline PTFE polymer and had a microstructure characterized by nodes interconnected by fibrils.

The FLUON CD123 resin is a white free-flowing powder made by coagulation of an aqueous dispersion of polytetrafluoroethylene (PTFE). It is designed for paste extrusion with volatile hydrocarbon lubricants for applications in which opacity in the sintered article is not a problem. FLUON CD123 has a relatively high molecular weight. Unsintered extrudates exhibit good green strength.

TYPICAL PROPERTIES OF FLUON CD 123

| Property | Nominal Value | Units | Test Method |
|---|---|---|---|
| Apparent Density | 500 | grams/liter | ASTM D 1457-83 |
| Median Particle Size | 500 | microns | ASTM D 1457-83 |
| Melting Point | 327 | ° C. | ASTM D 1457-83 |
| Color | White | | |
| Specific Gravity | 2.16–2.18 | | ASTM D 1457-83 |
| Moisture Content(Max.) | 0.04 | % | ASTM D 1457-83 |
| Extrusion Pressure | 15000 | psi | |

EXAMPLE 2

Example 1 was repeated except that twenty grams of ISOPAR M solvent was utilized instead of twenty-five grams and the pre-form charge was extruded at a reduction ratio (RR) of 91:1 into cylindrical thin-walled tubing. Approximately twenty feet of cylindrical tubing was produced.

EXAMPLE 3

Example 1 was repeated except that eighteen grams of ISOPAR M solvent was utilized instead of twenty-five grams and the pre-form charge was extruded at a reduction ratio (RR) of 48:1 into cylindrical thin-walled tubing. Approximately ton feet of thin-walled tubing was produced.

EXAMPLE 4

Example 1 was repeated except that eighteen grams of ISOPAR M solvent was utilized instead of twenty-five grams; ninety-five grams of CD123 was utilized instead of one hundred grams; five grams of CD509 was combined with the ISOPAR M solvent and the CD123; and, the resulting pre-form charges was extruded at a reduction ratio (RR) of 48:1 into cylindrical thin-walled tubing. Approximately ten feet of thin-walled tubing was produced.

The FLUON CD509 resin is a white, free-flowing powder made by coagulation of an aqueous dispersion of polytetrafluoroethylene (PTFE). It is designed for paste extrusion at medium to high reduction ratios where high sintering rates are desirable.

TYPICAL PROPERTIES OF FLUON CD 123

| Property | Nominal Value | Units | Test Method |
|---|---|---|---|
| Apparent Density | 500 | grams/liter | ASTM D 1457-83 |
| Median Particle Size | 500 | microns | ASTM D 1457-83 |
| Melting Point | 327 | ° C. | ASTM D 1457-83 |
| Color | White | | |
| Specific Gravity | 2.18–2.20 | | ASTM D 1457-83 |
| Moisture Content(Max.) | 0.04 | % | ASTM D 1457-83 |
| Extrusion Pressure | 8700 | psi | |

EXAMPLE 5

Three tubes approximately thirty-five centimeters long produced in Example 1 were each tested as follows.

An appropriate size angioplasty balloon catheter manufactured by Boston Scientific was placed in the inner lumen of the tube and was inflated with water with a standard MONARCH endoflater at a rate of approximately ten psi per second. Merit Medical manufacture the MONARCH endoflater. The balloon was about four centimeters long. As is well known, the balloon catheter is normally inserted in a blood vessel by first inserting a wire in a vessel; then inserting a vessel dilator along the wire into the vessel; removing the vessel dilator; inserting an introducer sleeve along the wire into the vessel; inserting the balloon; removing the introducer sleeve; inflating the balloon; deflating the balloon; removing the balloon; and removing the wire. A similar procedure was used while utilizing the balloon catheter to test the PTFE tubes of Example 1.

The balloon catheter did not apply an outward expansion force against the tube until the catheter was inflated under pressure with water. Inflation of the balloon (and the concomitant increase in inflation pressure) was stopped at predetermined pressure intervals of one or one-half atmosphere pressure to measure the outside diameter of each tube. Each tube was dilated until it burst.

The actual inflation pressure was observed on a digital pressure gauge and recorded. The percent dilatation was calculated by measuring the tubing outside diameter with digital calipers at each pressure interval and then using the following formula:

$$\% \text{ Dilatation} = [(D_d - D_i)/(D_i)] \times 100$$

where $D_i$ = initial tube diameter at pressure equal to zero $D_d$ = measured dilated tubing diameter.

From the raw data, REC (Radial Expansion Coefficient), REL (Radial Expansion Limit), and RER (Radial Expansion Ratio) were calculated and recorded along with the calculated reduction ratio to lubricant level ratio (RR/LL), where:

$P_{max}$ = Maximum Inflation Pressure $P_{burst}$ = Burst Inflation Pressure

%RD = Percent Radial Dilatation

REC = $(P_{max})/(\% \text{ RD at } P_{max})$ $REL = (P_{burst})/(\% \text{ RD at } P_{burst})$ $RER = (REC)/(REL)$ As used herein, a tube retains its structural integrity after being radially expanded as long as the tube requires the application of an increased inflation pressure before the amount of radial expansion of the tube increases. If a tube continues to expand when the amount of inflation pressure decreases, then the tube has lost its structural integrity. When the Pmax of a tube is exceeded, the tube loses its structural integrity. However, the loss in structural integrity results in degradations of physical properties which are significantly less than those which occur in prior art PTFE tubes. For example, at a percent dilatation of about 300% in Table I below, the tube still retains about 70% to 75% of its pre-dilatation tensile strength. Also, in Table I below, Tube No. 1 loses its structural integrity at an inflation pressure greater than 6.5 atm ($P_{max}$). In Tables II and III below, Tubes No. 2 and 3, respectively also lose their structural integrity at an inflation pressure greater than 6.5 atm (Pmax).

The following results were obtained for the three Example 1 tubes which were tested:

TABLE I

Tube No. 1
Tube No. 1 Measurements

| Measurement | Inflation Pressure (Atm) | Diameter (mm) | % Dilatation |
|---|---|---|---|
| 1 | 0 | 2.75 | — |
| 2 | 1 | 2.75 | 0 |
| 3 | 2 | 2.75 | 0 |
| 4 | 3 | 3.05 | 11 |
| 5 | 3.5 | 3.13 | 14 |
| 6 | 4 | 3.20 | 16 |
| 7 | 4.5 | 3.34 | 21 |
| 8 | 5 | 3.37 | 23 |
| 9 | 5.5 | 3.92 | 43 |
| 10 | 6 | 4.62 | 68 |
| 11 | 6.5 ($P_{max}$) | 5.34 | 94 |
| 12 | 4.5 ($P_{burst}$) | 12.12 | 341 |

REC = (6.5 atm × 14.7 psi/atm)/94% = 1.02 psi/%
REL = (4.5 atm × 14.7 psi/atm)/341% = 0.19 psi/%
RER = (1.02)/(0.19) = 5.4

TABLE II

Tube No. 2
Tube No. 2 Measurements

| Measurement | Inflation Pressure (Atm) | Diameter (mm) | % Dilatation |
|---|---|---|---|
| 1 | 0 | 2.67 | — |
| 2 | 1 | 2.67 | 0 |
| 3 | 2 | 2.87 | 7 |
| 4 | 3 | 3.02 | 13 |
| 5 | 3.5 | 3.02 | 13 |
| 6 | 4 | 3.17 | 19 |
| 7 | 4.5 | 3.23 | 21 |
| 8 | 5 | 3.40 | 27 |
| 9 | 5.5 | 3.64 | 36 |
| 10 | 6 | 4.77 | 79 |
| 11 | 6.5 ($P_{max}$) | 5.51 | 106 |
| 12 | 4.5 ($P_{burst}$) | 12.51 | 369 |

REC = (6.5 atm × 14.7 psi/atm)/106% = 0.90 psi/%
REL = (4.5 atm × 14.7 psi/atm)/369% = 0.18 psi/%
RER = (0.90)/(0.18) = 5.0

TABLE III

Tube No. 3
Tube No. 3 Measurements

| Measurement | Inflation Pressure (Atm) | Diameter (mm) | % Dilatation |
|---|---|---|---|
| 1 | 0 | 2.75 | — |
| 2 | 1 | 2.75 | 0 |
| 3 | 2 | 2.75 | 0 |
| 4 | 3 | 3.05 | 11 |
| 5 | 3.5 | 3.13 | 14 |
| 6 | 4 | 3.20 | 16 |
| 7 | 4.5 | 3.34 | 21 |
| 8 | 5 | 3.37 | 23 |
| 9 | 5.5 | 3.92 | 43 |
| 10 | 6 | 4.62 | 68 |
| 11 | 6.5 ($P_{max}$) | 5.34 | 94 |
| 12 | 4.5 ($P_{burst}$) | 12.97 | 372 |

REC = (6.5 atm × 14.7 psi/atm)/94% = 0.90 psi/%
REL = (4.5 atm × 14.7 psi/atm)/371% = 0.18 psi/%
RER = (0.90)/(0.18) = 5.7

EXAMPLE 6

Three tubes approximately thirty-five centimeters long produced in Example 2 were each tested utilizing the equipment and procedure described in EXAMPLE 5. The following results were obtained for the three Example 2 tubes tested.

TABLE IV

Tube No. 1
Tube No. 1 Measurements

| Measurement | Inflation Pressure (Atm) | Diameter (mm) | % Dilatation |
|---|---|---|---|
| 1 | 0 | 4.27 | — |
| 2 | 1 | 4.27 | 0 |
| 3 | 2 | 4.27 | 0 |
| 4 | 3 | 4.35 | 2 |
| 5 | 3.5 | 5.85 | 37 |
| 6 | 4 ($P_{max}$) | 9.08 | 113 |
| 7 | 2.5 ($P_{burst}$) | 16.39 | 284 |

REC = (4.0 atm × 14.7 psi/atm)/113% = 0.52 psi/%
REL = (2.5 atm × 14.7 psi/atm)/284% = 0.13 psi/%
RER = (0.52)/(0.13) = 4.0

TABLE V

Tube No. 2
Tube No. 2 Measurements

| Measurement | Inflation Pressure (Atm) | Diameter (mm) | % Dilatation |
|---|---|---|---|
| 1 | 0 | 4.74 | — |
| 2 | 1 | 4.74 | 0 |
| 3 | 2 | 4.74 | 0 |
| 4 | 3 | 5.49 | 16 |
| 5 | 3.5 | 7.09 | 50 |
| 6 | 4 ($P_{max}$) | 10.00 | 111 |
| 7 | 3 ($P_{burst}$) | 20.52 | 333 |

REC = (4 atm × 14.7 psi/atm)/111% = 0.53 psi/%
REL = (3 atm × 14.7 psi/atm)/333% = 0.13 psi/%
RER = (0.53)/(0.13) = 4.1

TABLE VI

Tube No. 3
Tube No. 3 Measurements

| Measurement | Inflation Pressure (Atm) | Diameter (mm) | % Dilatation |
|---|---|---|---|
| 1 | 0 | 4.83 | — |
| 2 | 1 | 4.83 | 0 |
| 3 | 2 | 4.83 | 0 |
| 4 | 3 | 5.23 | 8 |
| 5 | 3.5 | 6.00 | 24 |
| 6 | 4 ($P_{max}$) | 9.66 | 100 |
| 7 | 3 ($P_{burst}$) | 18.12 | 275 |

REC = (4 atm × 14.7 psi/atm)/100% = 0.59 psi/%
REL = (3 atm × 14.7 psi/atm/275% = 0.16 psi/%
RER = (0.59)/(0.16) = 3.7

EXAMPLE 7

Two tubes approximately thirty-five centimeters long produced in Example 3 were each tested utilizing the equipment and procedure described in EXAMPLE 5. The following results were obtained for the two tubes tested.

TABLE VII

Tube No. 1
Tube No. 1 Measurements

| Measurement | Inflation Pressure (Atm) | Diameter (mm) | % Dilatation |
|---|---|---|---|
| 1 | 0 | 6.04 | — |
| 2 | 1 | 6.28 | 4 |
| 3 | 1.5 | 6.45 | 7 |
| 4 | 2 | 6.79 | 12 |
| 5 | 2.5 | 7.15 | 18 |
| 6 | 3 | 7.39 | 22 |
| 7 | 3.5 | 8.33 | 38 |
| 8 | 4 ($P_{max}$) | 9.82 | 63 |
| 9 | 3.7 ($P_{burst}$) | 24.77 | 310 |

REC = (4.0 atm × 14.7 psi/atm)/63% = 0.93 psi/%
REL = (3.7 atm × 14.7 psi/atm)/310% = 0.18 psi/%
RER = (0.93)/(0.18) = 5.2

TABLE VIII

Tube No. 2
Tube No. 2 Measurements

| Measurement | Inflation Pressure (Atm) | Diameter (mm) | % Dilatation |
|---|---|---|---|
| 1 | 0 | 5.99 | — |
| 2 | 1 | 6.65 | 11 |
| 3 | 1.5 | 6.76 | 13 |
| 4 | 2 | 7.01 | 17 |
| 5 | 2.5 | 7.31 | 22 |
| 6 | 3 | 7.73 | 29 |
| 7 | 3.5 | 8.43 | 41 |
| 8 | 4 | 9.09 | 52 |
| 9 | 4.5 ($P_{max}$) | 11.17 | 86 |
| 10 | 3.9 ($P_{burst}$) | 25.62 | 328 |

REC = (4.5 atm × 14.7 psi/atm)/86% = 0.77 psi/%
REL = (3.9 atm × 14.7 psi/atm)/328% = 0.17 psi/%
RER = (0.77)/(0.17) = 4.5

EXAMPLE 8

Two tubes approximately thirty-five centimeters long produced in Example 4 were each tested utilizing the equipment and procedure described in EXAMPLE 5. The following results were obtained for the two tubes tested.

TABLE IX

Tube No. 1
Tube No. 1 Measurements

| Measurement | Inflation Pressure (Atm) | Diameter (mm) | % Dilatation |
|---|---|---|---|
| 1 | 0 | 5.94 | — |
| 2 | 1 | 6.40 | 8 |
| 3 | 1.5 | 6.55 | 10 |
| 4 | 2 | 7.02 | 18 |
| 5 | 2.5 | 7.58 | 28 |
| 6 | 3 | 9.51 | 60 |
| 7 | 3.5 ($P_{max}$) | 13.15 | 121 |
| 8 | 2.9 ($P_{burst}$) | 24.15 | 307 |

REC = (3.5 atm × 14.7 psi/atm)/121% = 0.43 psi/%
REL = (3.9 atm × 14.7 psi/atm)/328% = 0.14 psi/%
RER = (0.43/(0.14) = 3.1

TABLE X

Tube No. 2
Tube No. 2 Measurements

| Measurement | Inflation Pressure (Atm) | Diameter (mm) | % Dilatation |
|---|---|---|---|
| 1 | 0 | 5.90 | — |
| 2 | 1 | 6.41 | 9 |
| 3 | 1.5 | 6.89 | 17 |
| 4 | 2 | 7.09 | 20 |
| 5 | 2.5 | 7.83 | 33 |
| 6 | 3 | 8.34 | 41 |
| 7 | 3.5 | 9.90 | 68 |
| 8 | 4 ($P_{max}$) | 13.05 | 121 |
| 9 | 3.1 ($P_{burst}$) | 24.76 | 320 |

REC = (4 atm × 14.7 psi/atm)/121% = 0.49 psi/%
REL = (3.1 atm × 14.7 psi/atm)/320% = 0.14 psi/%
RER = (0.49)/(0.14) = 3.5

EXAMPLE 9

Example 5 is repeated, except that after measurements are made at each pressure interval which causes the tube to dilate, the pressure is reduced by about one atmosphere to give the tube an opportunity to contract and five minutes later the diameter of the tube is remeasured. For example, after measurement no. 4 in Table I, the pressure is reduced to two atmospheres and five minutes later the diameter of the tube is remeasured; after example 5 in Table I, the pressure is reduced to two and a half atmospheres and five minutes later the diameter of the tube is remeasured; etc. Each time the diameter of the tube is remeasured, the diameter of the tube is reduced by about 10% or less from the measurement made when the pressure was one atmosphere greater. For example, after measurement no. 4; (3.05 mm) is taken in Table I, the water pressure is reduced to two atmospheres, and the diameter of the tube is measured five minutes later, the diameter of the tube is 2.75 mm.

EXAMPLE 10

Example 1 is repeated except that the stretch rate is 10% per second instead of 100% per second.

EXAMPLE 11

Example 1 is repeated except that the stretch rate is 300% per second instead of 100% per second.

EXAMPLE 12

Example 1 is repeated except that the tube is stretched to three times its original length instead of four times its original length.

EXAMPLE 13

Example 1 is repeated except that the tube is stretched to six times its original length instead of four times its original length.

EXAMPLE 14

Example 5 is repeated utilizing tubes produced during Example 10. Similar results are obtained.

EXAMPLE 15

Example 5 is repeated utilizing tubes produced during Example 11. Similar results are obtained.

EXAMPLE 16

Example 5 is repeated utilizing tubes produced during Example 12. Similar results are obtained.

EXAMPLE 17

Example 5 is repeated utilizing tubes produced during Example 13. Similar results are obtained.

Having described my invention in such terms as to enable those skilled in the art to understand and practice it, and having identified the presently preferred embodiments thereof, the present invention should be understood. However, the scope of the present invention should not be limited by the Examples provided, but instead all modifications, variations or equivalents that are within the scope of the appended claim should be considered within the scope of the invention.

What is claimed is:

1. An assembly for treating a body vessel, comprising:
   a radially expandable stent, having an inner surface and an outer surface; and
   a tubular liner consisting of expanded polytetrafluoroethylene, having a microstructure characterized by nodes interconnected by fibrils, wherein the liner is positioned along a length of the stent, covering at least one of the inner and outer surfaces;
   wherein the assembly is permanently radially expandable in vivo from a first diameter to a larger second diameter, and wherein the tubular liner maintains structural integrity at the second diameter up to approximately 100% of the first diameter.

2. The assembly according to claim 1, wherein said tubular liner has a radial expansion coefficient of less than 2.0.

3. The assembly according to claim 1, wherein said tubular liner has a radial expansion coefficient of less than 1.7.

4. The assembly according to claim 1, wherein said tubular liner has a radial expansion coefficient of less than 1.5.

5. The assembly according to claim 1, wherein said tubular liner has a radial expansion coefficient of less than 1.0.

6. The assembly according to claim 1, wherein said tubular liner has a radial expansion coefficient of less than 30.

7. The assembly according to claim 1, wherein said tubular liner has a radial expansion coefficient of less than 2.

8. The assembly according to claim 1, wherein said tubular liner has a radial expansion coefficient of less than 10.

9. The assembly according to claim 1, wherein said tubular liner has a radial expansion coefficient of less than 5.

10. The assembly according to claim 1, wherein said tubular liner has a reduction ratio to lubricant level of about 5 or less.

11. The assembly according to claim 10, wherein said lubricant level is between 16 and 35%.

12. The assembly according to claim 10, wherein said lubricant level is between 16 and 35%.

13. The assembly according to claim 10, wherein said reduction ratio is less than 300:1.

14. The assembly according to claim 10, wherein said reduction ratio is less than 200:1.

15. The assembly according to claim 10, wherein said reduction ratio is less than 125:1.

* * * * *